(12) United States Patent
Vasan

(10) Patent No.: US 9,386,915 B2
(45) Date of Patent: Jul. 12, 2016

(54) DISPOSABLE, SELF-CONTAINED LARYNGOSCOPE AND METHOD OF USING SAME

(76) Inventor: Nilesh R. Vasan, Nichols Hills, OK (US)

( * ) Notice: Subject to any disclaimer, the term of this patent is extended or adjusted under 35 U.S.C. 154(b) by 302 days.

(21) Appl. No.: 12/847,915

(22) Filed: Jul. 30, 2010

(65) Prior Publication Data

US 2012/0029293 A1  Feb. 2, 2012

(51) Int. Cl.
*A61B 1/267* (2006.01)
*A61B 1/00* (2006.01)
*A61B 1/06* (2006.01)

(52) U.S. Cl.
CPC .............. *A61B 1/267* (2013.01); *A61B 1/00103* (2013.01); *A61B 1/0669* (2013.01); *A61B 1/0684* (2013.01)

(58) Field of Classification Search
CPC .............. A61B 1/267–1/2763; A61B 1/00165; A61B 1/0684; A61B 1/07; A61B 19/5202; A61B 2019/5206
USPC ......... 600/185–201, 208, 212, 223, 233, 235, 600/237–239, 245, 248
See application file for complete search history.

(56) References Cited

U.S. PATENT DOCUMENTS

| 583,830 | A | * | 6/1897 | Wiley | 242/375.3 |
|---|---|---|---|---|---|
| 2,070,820 | A | * | 2/1937 | Allyn | 600/196 |
| 3,507,272 | A | * | 4/1970 | Laerdal | 600/191 |
| 3,592,199 | A | * | 7/1971 | Ostensen | 600/198 |
| 3,595,222 | A | * | 7/1971 | Vellacott et al. | 600/197 |
| 3,598,113 | A | * | 8/1971 | Moore et al. | 600/199 |
| 3,638,644 | A | * | 2/1972 | Reick | 600/191 |
| 4,306,547 | A | * | 12/1981 | Lowell | 600/188 |
| 4,337,761 | A | * | 7/1982 | Upsher | 600/188 |
| 4,425,909 | A | * | 1/1984 | Rieser | 600/197 |
| 4,583,527 | A | * | 4/1986 | Musicant et al. | 600/195 |
| 4,592,343 | A | * | 6/1986 | Upsher | 600/193 |
| 4,799,485 | A | * | 1/1989 | Furey et al. | 600/193 |
| 4,905,669 | A | * | 3/1990 | Bullard et al. | 600/104 |
| 4,947,896 | A | * | 8/1990 | Bartlett | 600/187 |
| 5,060,633 | A | * | 10/1991 | Gibson | 600/193 |
| 5,261,392 | A | * | 11/1993 | Wu | 600/188 |
| 5,277,173 | A | * | 1/1994 | Cantele | 600/191 |
| 5,402,771 | A | * | 4/1995 | Pilling | 600/188 |
| 5,603,688 | A | * | 2/1997 | Upsher | 600/190 |
| 5,651,761 | A | * | 7/1997 | Upsher | 600/194 |

(Continued)

OTHER PUBLICATIONS

Katz, Steven H., Misplaced Endotracheal Tubes by Paramedics in an Urban Emergency Medical Services System, Annals of Emergency Medicine, Jan. 2001, pp. 32-37.

(Continued)

*Primary Examiner* — Eduardo C Robert
*Assistant Examiner* — Michelle C Eckman
(74) *Attorney, Agent, or Firm* — Dunlap Codding, P.C.

(57) ABSTRACT

The present invention is generally directed toward a laryngoscope having a handle, a rigid cylindrical tube, and an optical subassembly. The handle has a distal end and a proximate end. The tube is hollow and also has a distal end having a distal opening and a proximate end having a proximate opening. The optical subassembly includes a light source located within the handle, a power source located within the handle and in communication with the light source and a light carrier extending between the handle and the tube and in communication with the light source and providing light inside and along the entire length of the tube.

10 Claims, 3 Drawing Sheets

(56) References Cited

U.S. PATENT DOCUMENTS

| | | | | |
|---|---|---|---|---|
| 5,665,052 | A * | 9/1997 | Bullard | 600/194 |
| 5,688,224 | A * | 11/1997 | Forkey et al. | 600/200 |
| 5,716,329 | A | 2/1998 | Dieter | |
| 5,897,489 | A * | 4/1999 | Urbanowicz et al. | 600/185 |
| 6,080,105 | A * | 6/2000 | Spears | 600/212 |
| 6,083,151 | A * | 7/2000 | Renner et al. | 600/114 |
| 6,146,402 | A * | 11/2000 | Munoz | 606/194 |
| 6,176,824 | B1 * | 1/2001 | Davis | 600/178 |
| 6,471,643 | B1 * | 10/2002 | Henderson | 600/185 |
| 6,655,377 | B2 * | 12/2003 | Pacey | 128/200.26 |
| 6,666,819 | B2 * | 12/2003 | Heine et al. | 600/199 |
| 6,843,769 | B1 * | 1/2005 | Gandarias | 600/189 |
| 7,338,440 | B1 * | 3/2008 | Smith | 600/187 |
| 8,414,481 | B2 * | 4/2013 | Hakanen et al. | 600/196 |
| 8,663,099 | B2 * | 3/2014 | Tydlaska et al. | 600/186 |
| 2002/0068854 | A1 * | 6/2002 | Heine et al. | 600/199 |
| 2003/0092967 | A1 * | 5/2003 | Fourie et al. | 600/191 |
| 2003/0095781 | A1 * | 5/2003 | Williams | 385/146 |
| 2004/0079364 | A1 * | 4/2004 | Christopher | 128/200.26 |
| 2004/0133073 | A1 * | 7/2004 | Berci et al. | 600/112 |
| 2004/0210114 | A1 * | 10/2004 | Simon | 600/185 |
| 2004/0210115 | A1 * | 10/2004 | Ma et al. | 600/199 |
| 2005/0065543 | A1 * | 3/2005 | Kahle et al. | 606/190 |
| 2005/0251119 | A1 * | 11/2005 | Eaton et al. | 606/15 |
| 2006/0224045 | A1 | 10/2006 | Whipple | |
| 2007/0100211 | A1 * | 5/2007 | Selover et al. | 600/199 |
| 2008/0108877 | A1 * | 5/2008 | Bayat | 600/214 |
| 2009/0032016 | A1 * | 2/2009 | Law et al. | 128/200.26 |
| 2009/0182364 | A1 * | 7/2009 | Mettler, Jr. | 606/161 |
| 2010/0069722 | A1 * | 3/2010 | Shalman et al. | 600/193 |
| 2010/0121152 | A1 * | 5/2010 | Boedeker | 600/187 |
| 2010/0198017 | A1 * | 8/2010 | Raspallo | 600/190 |
| 2010/0298644 | A1 * | 11/2010 | Kleene | 600/188 |
| 2011/0060190 | A1 * | 3/2011 | Pecherer | 600/188 |
| 2011/0077466 | A1 * | 3/2011 | Rosenthal | 600/188 |
| 2013/0190568 | A1 * | 7/2013 | Hakanen et al. | 600/186 |
| 2013/0197313 | A1 * | 8/2013 | Wan | 600/202 |

OTHER PUBLICATIONS

Jones, James H., Emergency Physician-Verified Out-of-hospital Intubation: Miss Rates by Paramedics, ACAD Emeg Med, Jun. 2004, vol. 11, No. 6, pp. 707-709.

Allison, Michael, An Update on Airway Management in Emergency Medicine, AAEM/RSE News, CommonSense Nov./Dec. 2012, pp. 30-34.

Deakin, CD., Prehospital Management of the Traumatized Airway, European Journal of Emergency Medicine, Dec. 1996, vol. 3 Issue 4, pp. 233-243.

Bochicchio, GV., Is Field Intubation Useful?, Current Opinion in Critical Care, Dec. 2003; vol. 9 Issue 6, pp. 524-529.

Wang, HE, How many attempts are required to accomplish out-of-hospital endotracheal intubation?, Academic Emergency Medicine, Apr. 2006, vol. 13 Issue 4, pp. 372-377.

Cobas, MA, Prehospital Intubations and Mortality: a level 1 trauma center perspective, Anesthesia-Analgesia, Aug. 2009, vol. 109, No. 2, pp. 489-493.

Allison, Michael, An Update on Airway Management in Emergency Medicine, AAEM/RSA News, Resident Journal Review, CommonSense, p. 30-34 Nov./Dec. 2012.

Katz, Steven, Misplaced Endotracheal Tubes by Paramedics in an Urban Emergency Medical Services System, EMS/Original Contribution, Annals of Emergency Medicine, p. 32-37, Jan. 2001.

Jones, James H., Emergency Physician-Verified Out-of-hospital Intubation: Miss Rates by Paramedics, Acad Emerg Med, p. 707-709, vol. 11, No. 6, Jun. 2004.

Saving Lives on the Battlefield; A Joint Trauma System Review of Pre-Hospital Trauma Care in Combined Joint Operating Area—Afghanistan (CJOA-A) Executive Summary, TCCC Updates, p. 77-85, Journal of Special Operations Medicine, vol. 13, Edition 1/Spring 2013.

Mabry, Robert, An Analysis of Battlefield Cricothyrotomy in Iraq and Afghanistan, p. 17-23, Journal of Special Operations Medicine vol. 12, Edition 1/Spring 2012.

Gaither, Joshua B., Prevalence of Difficult Airway Predictors in Cases of Failed Prehospital Endotracheal Intubation, The Journal of Emergency Medicine, vol. 47, No. 3, pp. 294-300, 2014.

Mhyre, Jill M., The Unanticipated Difficult Intubation in Obstetrics, Society for Obstetric Anesthesia and Perinatology, vol. 112, No. 3, Mar. 2011.

Quinn, A.C., Failed tracheal intubation in obstetric anaesthesia; 2 yr national case—control study in the UK, British Journal of Anaesthesia 110 (1): 74-80 (2013) Advance Access publication Sep. 17, 2012.

Vasdev, Gurinder M., Management of the difficult and failed airway in obstetric anesthesia, Journal of Anesthesia 22:38-48, 2008.

Office Action Summary for U.S. Appl. No. 13/740,164 mailed Sep. 2, 2015.

* cited by examiner

DISPOSABLE, SELF-CONTAINED LARYNGOSCOPE AND METHOD OF USING SAME

REFERENCE TO PENDING APPLICATIONS

This application does not claim the benefit of any pending patent application.

REFERENCE TO MICROFICHE APPENDIX

This application is not referenced in any microfiche appendix.

BACKGROUND OF THE INVENTION

The present invention relates to a laryngoscope, more specifically, toward a disposable laryngoscope having a rigid cylindrical body for clearing, visualizing, and accessing, the intubation pathway.

A laryngoscope is used to assist with the placement of a tube into a patient's trachea to aid with the oxygenation of the patient. The prior art laryngoscope uses either a straight or curved blade that allows for the visualization of the patient's vocal cords which are used for locating the patient's larynx and subsequently the trachea. This reduces the risk of intubating the patient's esophagus which would cause air to be blown into the stomach, causing stomach distension and vomiting not to mention depriving the patient of oxygen, and possibly death.

The presence of blood, saliva, vomit secretions can interfere with the proper placement of the laryngoscope. Further, in emergency situations, the proper placement of the laryngoscope must be done in a quick and safe manner. However, despite good technique by the health care provider utilizing the laryngoscope described in the prior art, there is still a need for an improved laryngoscope that can be used in difficult or emergency situations in and out of a medical facility.

SUMMARY OF THE INVENTION

The present invention satisfies the needs discussed above. The present invention is generally directed toward a laryngoscope, more specifically, toward a disposable laryngoscope having a rigid cylindrical body for clearing and visualizing the intubation pathway to assist with the intubation of a patient in an emergency situation or a patient known for having difficult intubation capability.

One aspect of the present invention includes a laryngoscope having a handle, a cylindrical tube and an optical subassembly. The handle has distal and proximate ends and a cavity for the seating of the optical subassembly. Further, the handle can be configured in a bent or straight configuration. A bougie and a suction catheter can be included to create an emergency airway kit to be used by emergency medical services inside as well as outside of a medical facility, i.e. a hospital.

The cylindrical tube is hollow and also has distal and proximate ends. The proximate end of the handle is in communication with the proximate end of the tube. The optical subassembly is located within the handle and extends into the tube.

The tube also has openings located at its proximate and distal ends. These openings allow the healthcare provider to visualize the proper placement of the laryngoscope within the patient's mouth and throat. To aid with the insertion of the cylindrical tube, the distal opening is oriented at an angle relative to the vertical cross sectional plane of the tube.

The tube can be made from a metal, a transparent material or translucent material or a combination of the three. The transparent or translucent material will aid in the illumination of the tube along its entire length which will also aid in the proper placement thereof. This is important in those emergency situations where they be excessive bleeding and/or vomiting which may quickly come up the laryngoscope thereby not obstructing the light source. Further, a suction catheter can be used to assist with the removal of the excessive blood and/or vomit from the patient's airway.

One aspect of the optical subassembly includes a light source located within the handle, a power source such as one or more batteries located also within a handle and in communication with the light source. A light carrier such as a fiber optic cable is in communication with the light source and extends from the handle into the tube wherein it produces light so that the healthcare provider can see the tube and into the patient's mouth and throat to aid in the proper placement thereof. In difficult intubation patients or those in an emergency situation, the health care provider passes a bougie through the laryngoscope between the vocal cords and into the trachea. The laryngoscope is removed, and the endotracheal tube (which allows ventilation of the patient) is guided over the bougie into the trachea to gain safe and quick control of the patient's airway.

Another aspect of the present invention includes the tube as described above with the addition of a strip of protective material located along the tube proximate to its proximate end. The inclusion of this material is to protect the patient's teeth during use. The material can be made from a rubber or other flexible type of material.

Another aspect of the present invention includes the tube as described above further having side ports that can be used for suction and/or jet ventilation.

Another aspect of the present invention includes the laryngoscope tube as described above but is configured to be connectably attached through existing laryngoscope handles. This connection can be swivel and/or hinged and can be removable.

Another aspect of the present invention includes a method of using the laryngoscope tube as described above to secure the airway of a patient. In a difficult or emergency situation where the visualization of a patient's larynx is impaired, the medical provider holds the inventive laryngoscope by the handle and inserts the cylindrical tube into the patient's throat, looking through the cylindrical tube until the larynx is visualized. At that point, a bougie is inserted through the cylindrical tube between the patient's vocal cords and into the patient's trachea. The inventive laryngoscope is removed along the bougie, leaving the bougie in place. The bougie can then guide an endrotracheal tube into the patient's trachea. Once in place, the bougie is then removed and the endrotracheal tube can be used to ventilate the patient.

Upon reading the included description, various alternative embodiments will become obvious to those skilled in the art. These embodiments are to be considered within the scope and spirit of the subject invention, which is only limited by the claims which follow and their equivalents.

DESCRIPTION OF THE PREFERRED EMBODIMENTS

The present invention is generally directed toward a laryngoscope, more specifically, toward a laryngoscope having a rigid cylindrical body for clearing, visualizing, and accessing the intubation pathway.

Figure 1:
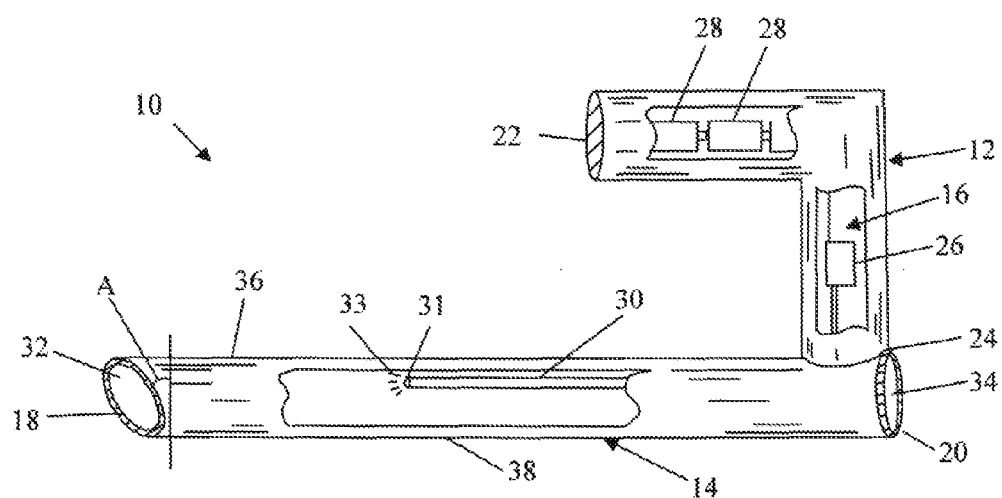
FIG. 1 is a side view of an embodiment of the present invention.

As shown in FIG. 1 the embodiment 10 of the inventive laryngoscope is illustrated. Embodiment 10 comprises a handle 12, a cylindrical tube 14 and an optical subassembly 16 contained within and extending between a handle 12 and cylindrical tube 14.

Figure 2:
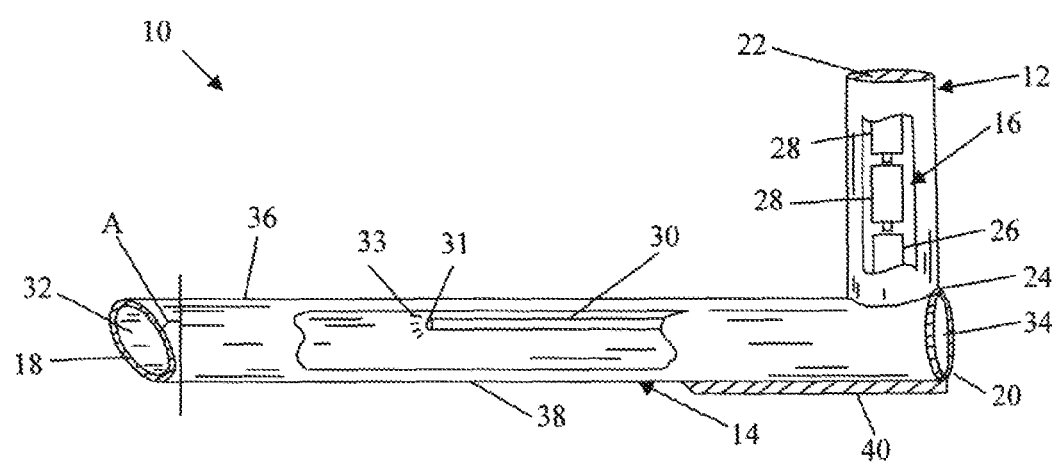
FIG. 2 is a side view of an additional embodiment of the present invention.

Handle 12 has a distal end 22 and a proximate end 24. Handle 12 can have a bent configuration as illustrated in FIG. 1 or a straight configuration as illustrated in FIG. 2.

Cylindrical tube 14 has a distal end 18 having a distal end opening 32 and a proximate end 20 having a proximate end opening. Distal end opening 32 is oriented at an angle relative to the vertical cross sectional plane of cylindrical tube 14. This angling of distal end opening 32 aids in the insertion of cylindrical tube 14 into the patient's mouth and throat. Cylindrical tube 14 is hollow to allow the user to view inside the patient's mouth and throat.

Proximate end 20 of cylindrical tube 14 is secured to the proximate end 24 of handle 12. The connection of cylindrical tube 14 and handle 12 can be of a unitary construction or of separate construction.

Optical subassembly 16 includes the light source 26 located within handle 12, a power source 28 located within handle 12 and in communication with light source 26. Power source 28 can include known power sources including batteries. A light carrier 30 is in communication with light source 26 and is located within handle 12 and extends into cylindrical tube 14. Light carrier 30 can include fiber optic cables, light emitting diodes (LEDs) or other similar devices. Light carrier 30 terminates within cylindrical tube 14. Light 33 emanates from the end 31 of light carrier 30. Light 33 illuminates the interior of the cylindrical tube 14 thereby aiding the user of embodiment 10 in placing the embodiment properly within the patient's mouth and throat.

Cylindrical tube 14 is rigid and can be made from a suitable metal, a transparent material, a translucent material or combination thereof. The use of transparent and/or translucent material can aid with the illumination of the entire cylindrical tube 14 along its length. This is useful in situations where blood or other items can hinder the ability to view the interior of the patient's mouth and/or throat. The laryngoscope may be of different lengths and widths.

The laryngoscope may be disposable (or single use), allowing its inclusion with a bougie and suction catheter into an emergency airway kit to be used by emergency medical services inside as well as outside of a medical (hospital) facility.

Once the inventive laryngoscope is placed properly within the patient's throat, various devices including a suction tube or a bougie (not shown) can be inserted through cylindrical tube 14 into the patient's trachea. When a bougie is inserted, the cylindrical tube 14 can then be removed by sliding such along the bougie, leaving the bougie in place. The bougie then acts a guide for the proper placement of additional devices such as an endotracheal tube to aid the patient.

Figure 3:
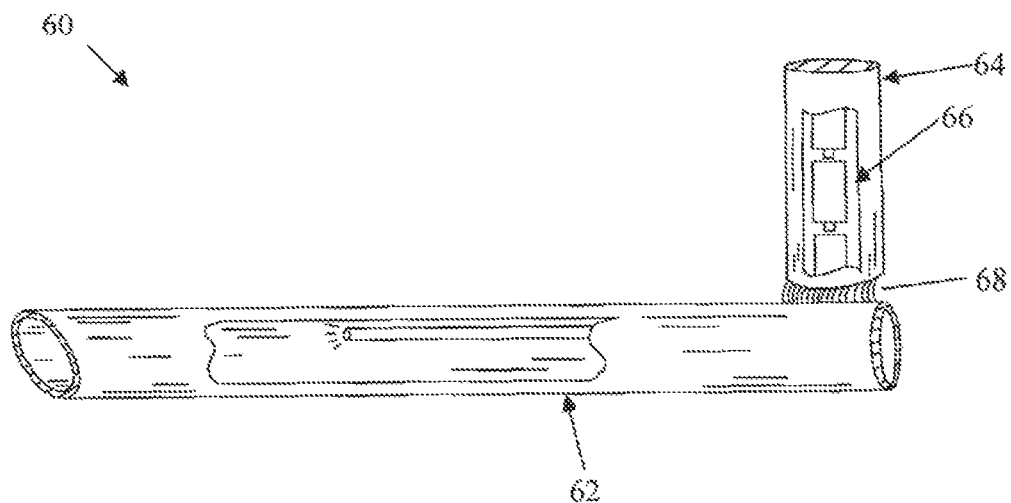
FIG. 3 is a side view of an additional embodiment of the present invention.

Another embodiment 60 of the present invention is illustrated in FIG. 3. This embodiment includes a cylindrical tube 62. Cylindrical tube 62 includes the same features as the cylindrical tube of the previous embodiment. Embodiment 60 also includes a handle 64 and an optical subassembly 66 that is located within handle 64. Handle 64 is hindgely connected to cylindrical tube 62 by a hinge 68. Hinge 68 is merely illustrative and is not limiting. Those schooled in the art would recognize other forms of moveable connections can be utilized with the present invention. Additionally tube 62 can include connection means not shown that can be configured to adapt to prior art laryngoscope handles.

Figure 4:
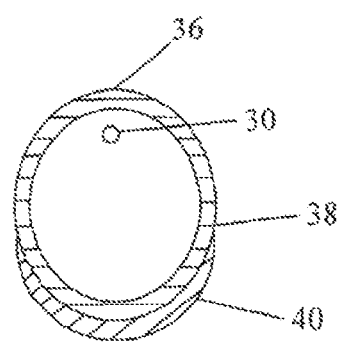
FIG. 4 is a front cross-sectional view of an embodiment of the cylindrical tube of the present invention.

An additional feature of the present invention is illustrated in FIGS. 2 and 4. This feature includes a strip of protective material 40 located along the outer side 38 of tube 14 near its proximate end 20. This protective material is utilized to protect the teeth and soft tissue located within the patient's mouth during use. The protective material 40 can be made from rubber or other suitable flexible material.

Another feature of the inventive laryngoscope can include a cylindrical tube 14 having one or more side ports not shown to allow for suction and/or jet ventilation.

Another embodiment of the present invention comprises a method of using the laryngoscope tube as described above to secure the airway of a patient. This embodiment includes holding the inventive laryngoscope by the handle, inserting the cylindrical tube into the patient's throat, looking through the cylindrical tube until the larynx is visualized. At that point, a bougie is inserted through the cylindrical tube between the patient's vocal cords and into the patient's trachea. The inventive laryngoscope is removed along the bougie, leaving the bougie in place. The bougie can then guide an endrotracheal tube into the patient's trachea. Once in place, the bougie is then removed and the endrotracheal tube can be used to ventilate the patient.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claims, including the full range of equivalency to which each element thereof is entitled.

We claim:

1. A disposable laryngoscope comprising:
   a handle having a distal end and a proximate end;
   a tube being made at least partially from a translucent material and having a sidewall that is continuous along its length from a distal end to a proximate end, with a straight longitudinal axis between the distal end and the proximate end allowing for a straight line of sight through the tube to view the inside of a patient's mouth and throat, the distal end being open with the opening being oriented at an angle relative to the vertical cross-sectional plane of the tube and the proximate end of the tube being open and secured to the proximate end of the handle; and
   an optical subassembly mounted within the handle having a light emitting diode which communicates with a light carrier extending from the handle through the sidewall of the tube at its proximate end and downwardly through the tube toward the distal end, terminating at a position within the tube remote from the distal end to thereby disperse light and illuminate the tube interior from its proximate end to its distal end to assist with the view of the patient's mouth and throat.

2. The laryngoscope of claim 1 wherein the optical subassembly further comprises:

a power source in communication with the light emitting diode.

3. The laryngoscope of claim 1 wherein at least a portion of the tube is made from a metal.

4. The laryngoscope of claim 1 wherein the tube is made from a transparent material.

5. The laryngoscope of claim 1, wherein the tube is made from a combination of two or more materials selected from the group consisting of metal, transparent material and translucent material.

6. The laryngoscope of claim 1, further comprising a strip of protective material located on the tube proximate the proximate end of the tube.

7. The laryngoscope of claim 1, wherein the handle has a bent configuration.

8. The laryngoscope of claim 1, wherein the handle has a straight configuration.

9. A laryngoscope for use with a handle, said handle having a distal end and a proximate end and an optical subassembly contained therein, said laryngoscope comprising:
- a tube being made at least partially from a translucent material and having a sidewall that is continuous along its length from a distal end to a proximate end, with a straight longitudinal axis between the distal end and the proximate end allowing for a straight line of sight through the tube to view the inside of a patient's mouth and throat, the distal end being open with the opening being oriented at an angle relative to the vertical cross-sectional plane of the tube, and the proximate end of the tube being in hinged communication with the proximate end of the handle; and
- said optical subassembly having a light emitting diode and a light carrier extending from the handle through the sidewall of the tube and terminating at a position within the tube remote from its distal end whereby light is dispersed from the terminal end of the light carrier into the translucent material of the tube which illuminates the tube interior from its proximate end to its distal end to assist with viewing of the patient's mouth and throat.

10. A method for securing the airway of a patient in a difficult or emergency situation where visualization of the patient's larynx is impaired, and the situation requires using a laryngoscope comprising a handle having a distal end and a proximate end; a tube having a sidewall made at least partially from a length of translucent material, said tube being continuous along its length and having an open distal end and an open proximate end, with a straight longitudinal axis between the distal end and the proximate end allowing for a straight line of sight through the length of the tube to view the inside of a patient's mouth and throat, the distal opening being oriented at an angle relative to the vertical cross-sectional plane of the tube, the proximate end of the tube being secured to the proximate end of the handle; and an optical subassembly mounted in the handle having a light emitting diode which communicates with a light carrier extending from the handle through the sidewall of the tube adjacent the handle and downwardly through the tube, terminating at a position within the tube remote from the distal end whereby light is dispersed from the terminal end of the light carrier into the translucent material of the tube, said method comprising the following steps:

- engaging the optical subassembly thereby providing illumination of the translucent material along the interior length of the tube to thereby assist with the viewing of the patient's mouth and throat;
- holding the laryngoscope by the handle;
- inserting the cylindrical tube into the patient's throat;
- looking in a straight line of sight through the proximate opening of the cylindrical tube through to the distal opening of the cylindrical tube until the larynx is visualized;
- inserting a bougie through the cylindrical tube between the patient's vocal cords and into the patient's trachea;
- removing the laryngoscope by passing the cylindrical tube along the bougie, leaving the bougie in place;
- guiding an endotracheal tube along the bougie until the endotracheal tube is inserted into the patient's trachea;
- removing the bougie;
- using the endotracheal tube to ventilate the patient; and
- disposing of the cylindrical tube.

\* \* \* \* \*